US011439719B2

(12) United States Patent
Lucio

(10) Patent No.: US 11,439,719 B2
(45) Date of Patent: Sep. 13, 2022

(54) DEVICE FOR DISINFECTING EQUIPMENT AND METHOD OF USING THE SAME

(71) Applicant: 3B Medical, Inc., Winter Haven, FL (US)

(72) Inventor: Albert A. Lucio, Haines City, FL (US)

(73) Assignee: 3B Medical, Inc., Winter Haven, FL (US)

( * ) Notice: Subject to any disclaimer, the term of this patent is extended or adjusted under 35 U.S.C. 154(b) by 236 days.

(21) Appl. No.: 16/833,799

(22) Filed: Mar. 30, 2020

(65) Prior Publication Data

US 2020/0222568 A1    Jul. 16, 2020

Related U.S. Application Data

(63) Continuation-in-part of application No. 15/956,793, filed on Apr. 19, 2018.

(60) Provisional application No. 62/500,648, filed on May 3, 2017.

(51) Int. Cl.
*A61L 2/26* (2006.01)
*A61L 2/20* (2006.01)
*A61L 2/10* (2006.01)
*A61L 2/06* (2006.01)

(52) U.S. Cl.
CPC .............. *A61L 2/26* (2013.01); *A61L 2/06* (2013.01); *A61L 2/10* (2013.01); *A61L 2/202* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/16* (2013.01); *A61L 2202/24* (2013.01)

(58) Field of Classification Search
CPC ..... A61L 2/26; A61L 2/06; A61L 2/10; A61L 2/202; A61L 2202/11; A61L 2202/121; A61L 2202/122; A61L 2202/14; A61L 2202/15; A61L 2202/16; A61L 2202/24; A61L 2/24; A61M 16/00
See application file for complete search history.

(56) References Cited

U.S. PATENT DOCUMENTS

| | | | |
|---|---|---|---|
| 5,979,472 A | 11/1999 | Lowery et al. | |
| 6,555,053 B1 * | 4/2003 | Aoyagi | A61L 9/03 422/5 |
| 7,326,387 B2 * | 2/2008 | Arts | A61L 2/10 422/186.3 |
| 7,959,872 B2 * | 6/2011 | Namespetra | C02F 1/78 422/300 |
| 8,048,370 B1 * | 11/2011 | Barnes | A61L 9/20 422/4 |

(Continued)

*Primary Examiner* — Regina M Yoo
(74) *Attorney, Agent, or Firm* — Carlson, Gaskey & Olds, P.C.

(57) ABSTRACT

This disclosure relates to a device for disinfecting equipment, such as medical devices, surgical equipment, and/or CPAP components (or, CPAP equipment), including the various parts of a CPAP system, such as hoses, masks, pillows, couplings, humidifiers, etc., that require frequent cleaning and disinfecting. An example device includes a chamber, an ultraviolet (UV) light configured to emit UV light within the chamber, an ozone generator configured to generate ozone within the chamber, and a control unit configured to activate the UV light and the ozone generator simultaneously for a first period of time. A method is also disclosed.

14 Claims, 5 Drawing Sheets

(56) References Cited

U.S. PATENT DOCUMENTS

| | | | |
|---|---|---|---|
| 8,898,929 B2* | 12/2014 | Stewart | D06F 59/04 |
| | | | 34/381 |
| 9,107,973 B1 | 8/2015 | Robinson et al. | |
| 9,205,162 B2 | 12/2015 | Deal et al. | |
| 10,874,756 B1* | 12/2020 | Guerrero | A61L 2/10 |
| 2007/0093387 A1 | 4/2007 | Sumi et al. | |
| 2008/0159907 A1* | 7/2008 | Joshi | A61L 2/202 |
| | | | 422/5 |
| 2010/0329924 A1 | 12/2010 | Harris | |
| 2014/0271348 A1 | 9/2014 | Deal et al. | |
| 2014/0319374 A1 | 10/2014 | Chandler | |
| 2017/0136136 A1 | 5/2017 | Li et al. | |
| 2017/0165386 A1 | 6/2017 | Huang | |
| 2020/0360551 A1* | 11/2020 | Naito | F24F 3/163 |

* cited by examiner

DEVICE FOR DISINFECTING EQUIPMENT AND METHOD OF USING THE SAME

RELATED APPLICATIONS

This application is a continuation-in-part of U.S. application Ser. No. 15/956,793, filed Apr. 19, 2018, which claims the benefit of U.S. Provisional Application No. 62/500,648, filed May 3, 2017. The '793 and '648 applications are herein incorporated by reference in their entirety.

TECHNICAL FIELD

This disclosure relates to a device for disinfecting equipment, such as CPAP components, and a method of using the same.

BACKGROUND

Continuous positive airway pressure (CPAP) represents a treatment for patients with breathing problems. Such problems typically manifest themselves at night while the patient is asleep. One such problem is sleep apnea.

The CPAP treatment uses mild air pressure to keep airways open, particularly when a patient is sleeping. CPAP systems have several components. The first is a flow generator, which is essentially a pump that creates a stream of air. Many flow generators include a humidifier, which is typically attached to the flow generator or integrally formed with the same. Humidifiers are configured to heat and moisten the air flow from the flow generator, which reduces the likelihood that a patient will experience discomfort from breathing dry air for a prolonged period. CPAP systems also include a conduit (i.e., a tube or hose) fluidly coupling a mask apparatus to the flow generator. The mask is affixed to the mouth and/or nose of a patient. CPAP systems also include various couplings, fittings, seals, valves, etc., that establish the fluid connection between the flow generator and the patient.

During use over the course of days, weeks, and months, it is recommended that the components of a CPAP system be cleaned and disinfected to prevent buildup of bacteria, for example. Disinfection is recommended to reduce health risks. CPAP systems and their associated components are typically cleaned manually by a patient using soap and water.

SUMMARY

A device for disinfecting equipment according to an exemplary aspect of the present disclosure includes, among other things, a chamber, an ultraviolet (UV) light configured to emit UV light within the chamber, an ozone generator configured to generate ozone within the chamber, and a control unit configured to activate the UV light and the ozone generator simultaneously for a first period of time.

In a further non-limiting embodiment of the foregoing device, the first period of time is seven minutes.

In a further non-limiting embodiment of any of the foregoing devices, the UV light emits UV-C light.

In a further non-limiting embodiment of any of the foregoing devices, the UV light emits UV light at a wavelength of 254 nanometers (nm).

In a further non-limiting embodiment of any of the foregoing devices, the UV light includes a 13 Watt UV-C bulb.

In a further non-limiting embodiment of any of the foregoing devices, the device includes a blower, and the control unit configured to activate the blower for the first period of time.

In a further non-limiting embodiment of any of the foregoing devices, the device includes a heater, and, after the first period of time, the control unit is configured to activate the heater and the blower for a second period of time.

In a further non-limiting embodiment of any of the foregoing devices, the control unit is configured to activate the heater to raise a temperature of the chamber to a predetermined temperature and to maintain the chamber at the predetermined temperature for a second period of time.

In a further non-limiting embodiment of any of the foregoing devices, the second period of time is seven minutes.

In a further non-limiting embodiment of any of the foregoing devices, the device includes a vacuum pump, and, after the second period of time, the controller is configured to deactivate the heater and activate the blower for a third period of time. Further, the controller is configured to activate the vacuum pump during the third period of time.

In a further non-limiting embodiment of any of the foregoing devices, the vacuum pump is activated near an end of the third period of time.

In a further non-limiting embodiment of any of the foregoing devices, the device includes a base, and a closure moveable relative to the base between an open position and a closed position. The base and closure provide boundaries of the chamber when the closure is in the closed position.

In a further non-limiting embodiment of any of the foregoing devices, the closure is lockable relative to the base and is only unlocked when one or both of a temperature of the chamber and a level of ozone within the chamber are below predetermined thresholds.

In a further non-limiting embodiment of any of the foregoing devices, the device includes a temperature sensor, an ozone sensor, and the controller is configured to interpret signals of the temperature sensor and the ozone sensor to determine a temperature of the chamber and a level of ozone within the chamber, respectively.

In a further non-limiting embodiment of any of the foregoing devices, the closure is only unlocked when there is no detectable level of ozone within the chamber.

In a further non-limiting embodiment of any of the foregoing devices, the chamber has a volume of 7.5 cubic feet.

In a further non-limiting embodiment of any of the foregoing devices, equipment is within the chamber, and wherein the equipment includes at least one of CPAP components, medical devices, and surgical instruments.

A method for disinfecting equipment according to an exemplary aspect of the present disclosure includes, among other things, emitting ultraviolet (UV) light within a chamber containing a piece of equipment for a first time period, and generating ozone within the chamber for the first time period.

In a further non-limiting embodiment the foregoing method, after the first time period, heating the chamber for a second time period.

In a further non-limiting embodiment of any of the foregoing methods, after the second time period, cooling the chamber and evacuating the chamber.

BRIEF DESCRIPTION OF THE DRAWINGS

In FIG. 1, a lid of the device is in an open position.

In FIG. 3, the drawer of the device is in a closed position.

DETAILED DESCRIPTION

This disclosure relates to a device for disinfecting equipment, such as medical devices, surgical equipment, and/or CPAP components (or, CPAP equipment), including the various parts of a CPAP system, such as hoses, masks, pillows, couplings, humidifiers, etc., that require frequent cleaning and disinfecting. An example device includes a chamber, an ultraviolet (UV) light configured to emit UV light within the chamber, an ozone generator configured to generate ozone within the chamber, and a control unit configured to activate the UV light and the ozone generator simultaneously for a first period of time.

Figure 1:
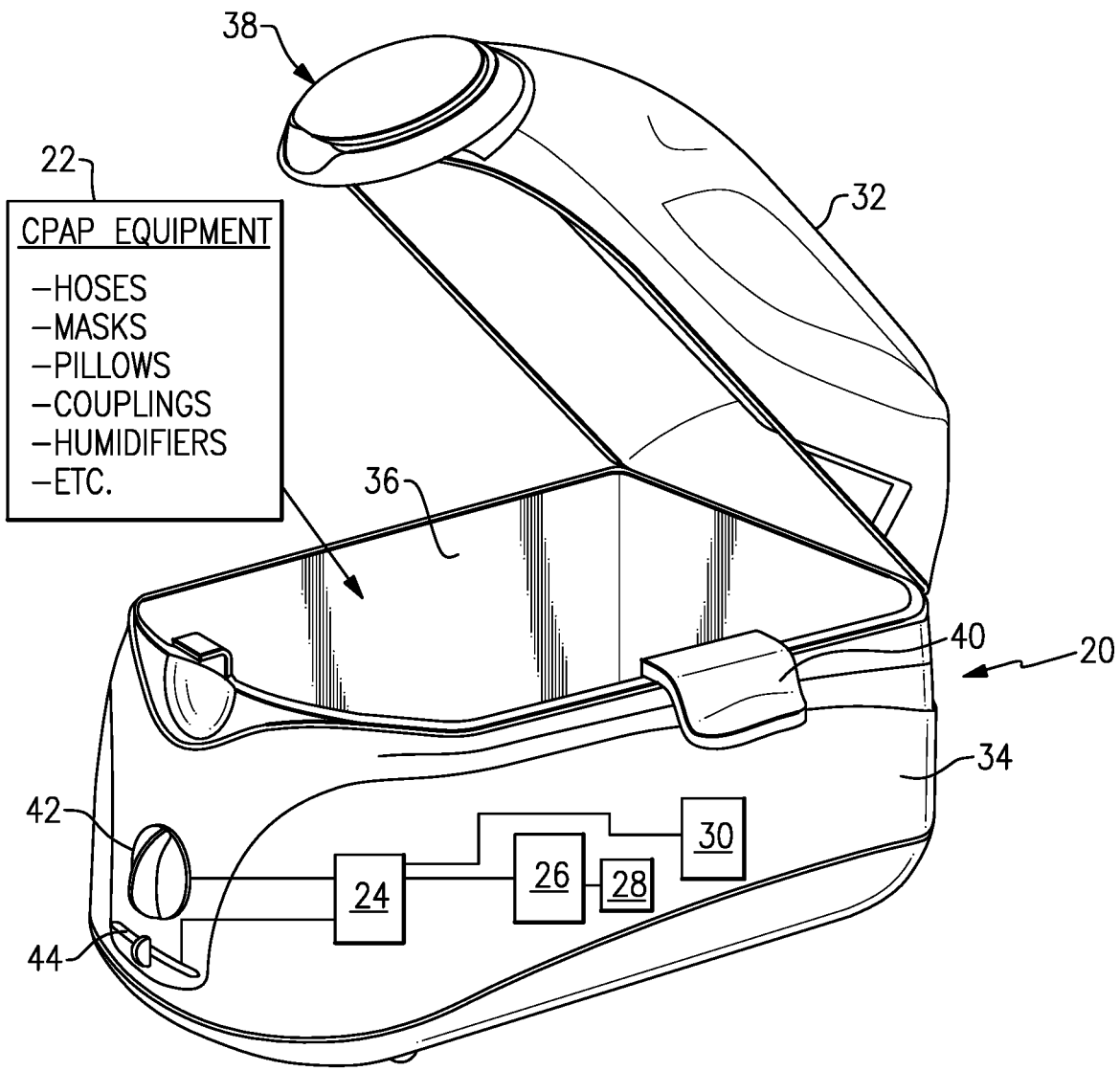
FIG. 1 illustrates an example device for disinfecting CPAP components from a perspective view. Certain aspects of the device are illustrated schematically.
Figure 2:
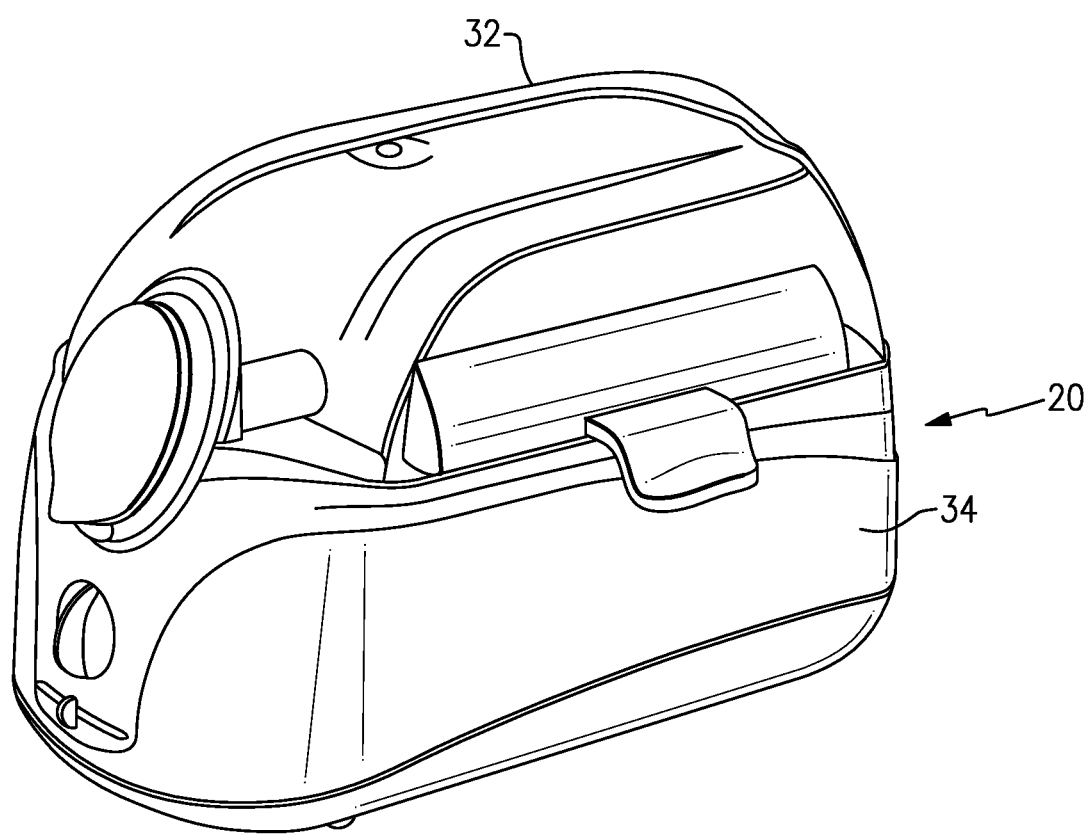
FIG. 2 illustrates the device of FIG. 1 with the lid in a closed position.

FIGS. 1 and 2 illustrate an example device 20 for disinfecting CPAP components 22 from a perspective view. In the embodiment of FIGS. 1 and 2, the device 20 includes a number of customizable operating parameters, which may be set by the user, as will be discussed below. The device 20 may be particularly useful in laboratory settings, where users are trained to set these parameters. This disclosure also relates to a device, such as that described relative to FIGS. 3 and 4, which does not allow a user to set any operating parameters. The latter device may be more user friendly from the perspective of some users, and may be more applicable for residential applications.

With continued reference to FIGS. 1 and 2, the device 20 includes a control unit 24, heater 26, blower (e.g., fan) 28, and an ultraviolet (UV) light 30. It should be understood that the CPAP components 22, control unit 24, heater 26, blower 28, and UV light 30 are illustrated schematically.

The control unit (sometimes called a "controller") 24 may be programmed with executable instructions for interfacing with and operating the various components of the device 20, including but not limited to those shown in the figures and discussed herein. It should also be understood that the control unit 24 may additionally include a combination of hardware and software, and specifically may include a processing unit and non-transitory memory for executing the various control strategies and modes of the device 20.

The UV light 30 is selectively activated in response to instructions from the control unit 24. The UV light 30 in this example is provided by a light source, specifically a UV bulb (sometimes called a "UV lamp"), which is configured to emit UV light. The UV light 30 may be provided by a 13 Watt UV-C bulb, in one example. In other examples, the UV light 30 is provided by a bulb within a range of 5 to 20 Watts.

In a particular example, the UV light 30 is configured to emit UV-C light, which is a subtype of UV light especially suited for disinfection. Specifically, UV-C is relatively short-wavelength UV light, which is known to kill or inactivate microorganisms such as bacteria. In one example, the UV light 30 emits UV light at a wavelength within a range of 250 to 270 nanometers (nm), and in one particular example the UV light has a wavelength of 254 nm.

The device 20 includes a lid 32 pivotably mounted to a base 34 and configured to pivot between an open position (FIG. 1) and a closed position (FIG. 2). In the open position, one or more CPAP components 22 can be provided into a chamber 36 within the device. The chamber 36 is partially defined by the lid 32 and partially defined by the base 34. When the lid 32 is closed, the lid 32 and base 34 define an enclosed chamber 36. The control unit 24 is configured to determine when the lid 32 is closed, such as in response to a signal from a sensor, such as a magnetic switch. The lid 32 and base 34 are sized such that the chamber 36 can hold a number of pieces of CPAP components.

The lid 32 is held in place in the closed position by way of a handle 38, which includes a latch, and one or more clasps 40. In this example, there is only one clasp 40 on a side of the base 34, but it should be understood that the device 20 could include additional clasps 40. Further, the lid 32 and 34 are sized and arranged such that, when the lid 32 is in the closed position, a seal is established. During use of the device 20, there may be relatively hot air flowing within the chamber 36. The handle 38 (which includes a latch) and clasp 40 ensures that the lid 32 stays closed and sealed during operation.

In one example, when the lid 32 is in the closed position, the chamber 36 can hold at least a humidifier, hose, and mask. This disclosure is not limited to these CPAP components 22, and can be used to disinfect other pieces of CPAP components 22, including but not limited to hoses, masks, pillows, humidifiers, couplings, fittings, seals, valves, etc. To this end, this disclosure is not even limited to use with CPAP components. For instance, the device 20 can be used to disinfect other medical, dental, and hygiene-related products, such as toothbrushes, hearing aids, dentures, pacifiers, etc.

Operation of the device 20 is regulated by the control unit 24, which is electrically coupled in this example to a first dial 42, a second dial 44, the heater 26, the blower 28, and the UV light 30.

The first dial 42 is a rotatable knob and is configured to control a temperature setting in one example. The control unit 24 is configured to interpret the input from the first dial 42, and regulate operation of the heater 26 (which could be any known type of heater, such as a coil heater) and blower 28 accordingly. The second dial 44 is an adjustable slider and is configured to control a time setting in one example. The control unit 24 is configured to interpret the input from the second dial 44 and operate the heater 26, blower 28, and UV light 30 for the set time. It should be understood that the first and second dials 42, 44 could be different types of input devices, and are not limited to knobs and sliders.

In one example process, a user places CPAP components 22 within the chamber 36 and closes the lid 32. In the example of FIG. 1, the user sets the first dial 42 and second dial 44, and presses an "on" button. Alternatively, there is no "on" button and the process begins automatically when the lid 32 is closed.

The control unit 24 is configured to instruct the heater 26 to heat air within the chamber 36, and the control unit 24 is further configured to activate the blower 28 and UV light 30. The blower 28 distributes heated air through the chamber 36 and evenly heats the CPAP components 22 using convection. During this process, the UV light 30 emits ultraviolet light to kill or inactivate the microorganisms and bacteria within the chamber 36.

In one example, the heater 26 is responsive to instructions from the control unit 24 such that the chamber 36 reaches a temperature of about 190° F. (about 88° C.) for about 3 minutes. In another example, the period of time is about 5 minutes. In other examples, the temperature is above about 140° F., which is a temperature above which most bacteria are killed. Such a combination of heat, time, and exposure to UV light disinfects the CPAP components 22 without damaging the same. In one example, about 99% of all microorganisms and bacteria are killed or inactivated through use of the device 20. In other examples, however, the device 20 does not include the heater 26 or the blower 28, and instead the control unit 24 activates the UV light 30 for the period of time. Without the heater 26 or the blower 28, the period of time may be longer than 3 minutes, such as about 5 minutes.

While first and second dials 42, 44 are shown, in another example, the control unit 24 is pre-programmed to operate disinfection cycle. In one particular example, the control unit 24 is pre-programmed to operate the heater 26, blower 28, and UV light 30 for a predefined period of time and at predefined levels. In this alternate example, a patient would simply close the lid 32 and depress an "on" button, if present, at which point the control unit 24 to begin the pre-defined disinfecting cycle.

Figure 3:
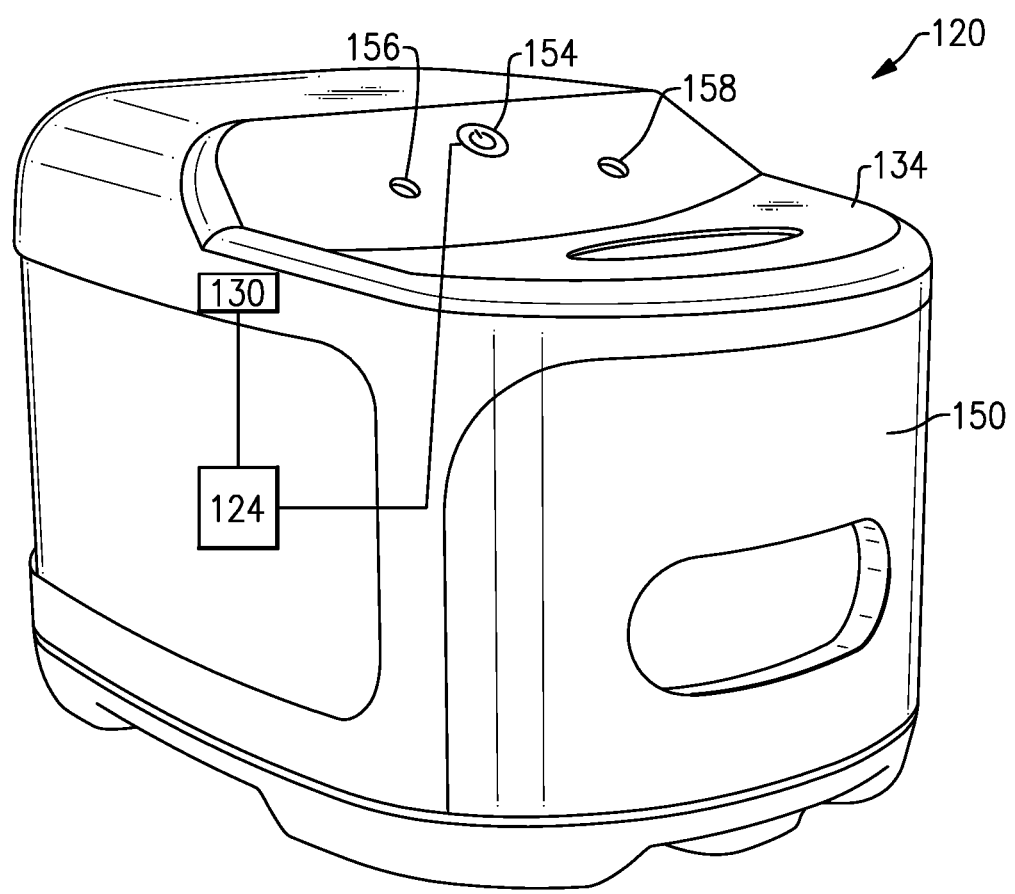
FIG. 3 illustrates another example device for disinfecting CPAP components from a perspective view.
Figure 4:
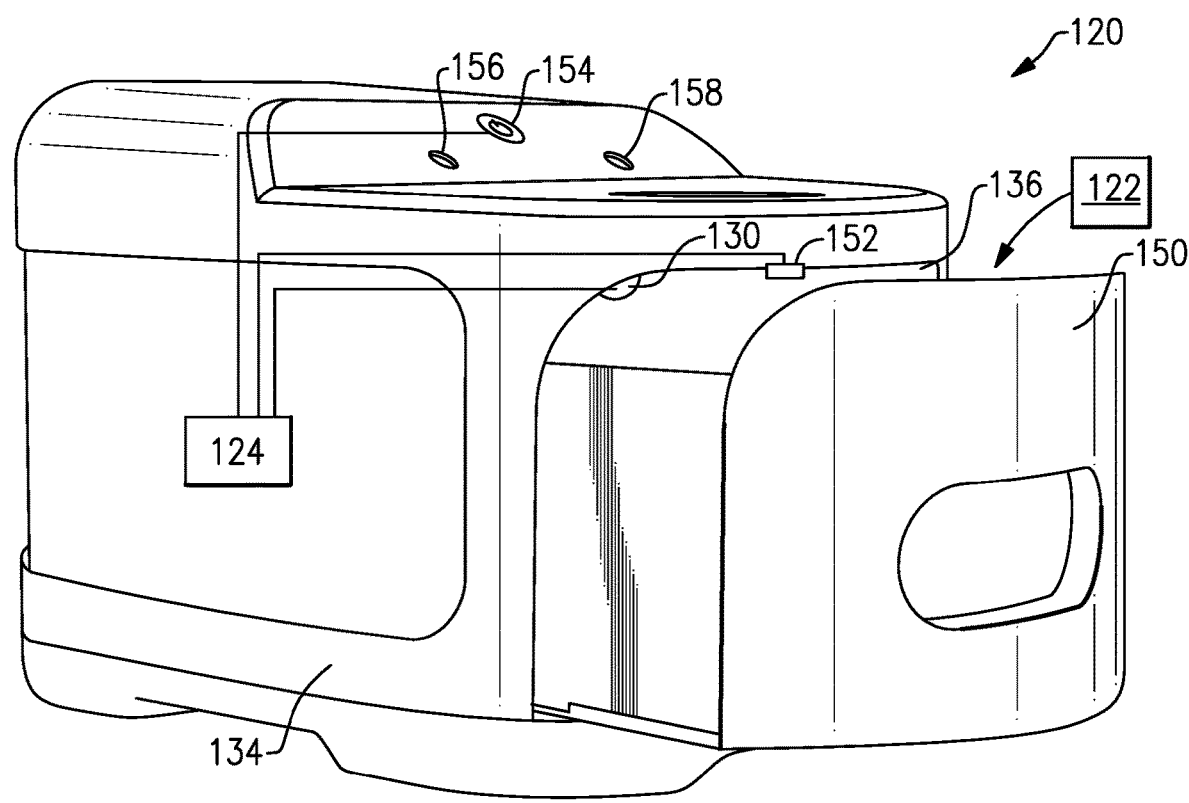
FIG. 4 illustrates the device of FIG. 3 with the drawer in the open position.

FIGS. 3 and 4 illustrate an example device 120 configured to disinfect CPAP components 122 (FIG. 4). To the extent not otherwise described or shown, the device 120 in FIGS. 3 and 4 corresponds to the device 20 of FIGS. 1 and 2, with like parts having reference numerals preappended with a "1."

Whereas the device 20 of FIGS. 1 and 2 may be particularly useful in a laboratory setting, the device 120 may be particularly useful in residential applications. In particular, the device 120 includes a control unit 124 that is pre-programmed to run a disinfection cycle when a user depresses an "on" button, and when the chamber 136 is closed. The control unit 124 is pre-programmed to run for a set time, which is a predefined period of time. In one example, the predefined period of time is about 5 minutes. The device 120 does not require the user to set any operating parameters of the disinfection cycle, and instead merely requires the user to insert their CPAP components 122 (FIG. 4) into the chamber 136, close the chamber 136, and press the "on" button.

The device 120 includes a base 134 and a drawer 150 slidably mounted to the base 134 and moveable relative to the base 134 between an open position (FIG. 4) and a closed position (FIG. 3). The base 134 and drawer 150 provide boundaries of the chamber 136 when the drawer 150 is in the closed position. The control unit 124 is configured to determine when the drawer 150 is closed, such by interpreting a signal from a sensor. One example sensor is a magnetic switch 152. The magnetic switch 152 may also serve to hold the drawer 150 in the closed position.

In one example, in order to increase the safety of the device 120, the control unit 124 only activates the UV light 130 when the drawer 150 is closed. If a user opens the drawer 150 mid-cycle, for example, the control unit 124 is configured to turn off the UV light 130.

Unlike the device 20, the device 120 does not include a heater or a blower. Rather, disinfection is performed solely by the UV light 130. In order to increase the reach of the UV light 130, the interior of the drawer 150 may be lined with a reflective material, such as polished aluminum. In this way, the UV light emitted by the UV light 130 is reflected within the chamber 136, which increases the surface area of the components 122 exposed to UV light.

As mentioned, the device 120 is configured to run a predefined disinfection cycle. To this end, the device 120 includes a button 154, which is an "on"/"off" button, a first status light 156, and a second status light 158. The first and second status lights 156, 158 may be replaced by a single status light in some examples. The button 154 and the status lights 156, 158 are electrically coupled to the control unit 124.

In one example disinfection cycle, a user opens the drawer 150, as shown in FIG. 4. The user then inserts one or more CPAP components 122 into the chamber 136. The user then shuts the drawer 150, as shown in FIG. 3, and depresses the button 154 to turn on the disinfection cycle. The control unit 124 is configured to determine that the drawer 150 is closed by way of a signal from the magnetic switch 152. When the drawer 150 is confirmed closed, the control unit 124 activates the UV light 130, which then emits UV light, and in particular emits UV-C light, such as that discussed above, for a predefined period of time. As above, the predefined period of time is about five (5) minutes. This period of time is set in a factory setting and stored on the control unit 124. In this example, the user is not allowed to change the predefined period of time.

During the disinfection cycle, the control unit 124 is configured to illuminate the first status light 156. The first status light 156 may be a red light, which indicates that the cycle is ongoing and should not be interrupted. After the predefined period of time, the control unit 124 deactivates the UV light 130, deactivates the first status light 156, and activates the second status light 158, which may be a green light indicating that the disinfection cycle is complete. Optionally, the base 134 may include a tinted lens 160 to allow a user to see into the chamber 136 during the disinfection cycle, while filtering the UV light.

The devices 20, 120 provide a reliable, quick, and relatively easy solution for cleaning and disinfecting CPAP components. The ease of use of the devices 20, 120, coupled with the relatively fast process, relieves a burden on patients faced with cleaning CPAP components on a regular basis. The devices 20, 120 are also less expensive than other higher cost systems on the market, such as those including air purifiers and ozone (which can be a lung irritant), those including ethylene oxide (which is dangerous), and those including chemical bactericides.

While ozone may be a lung irritant, it can be an effective disinfectant when used in a controlled setting by trained professionals. While the above-described embodiments do not use ozone, an aspect of this disclosure does use ozone as a disinfectant. This aspect of the disclosure may be used in controlled settings, such as laboratories and/or hospitals, as examples.

Figure 5:
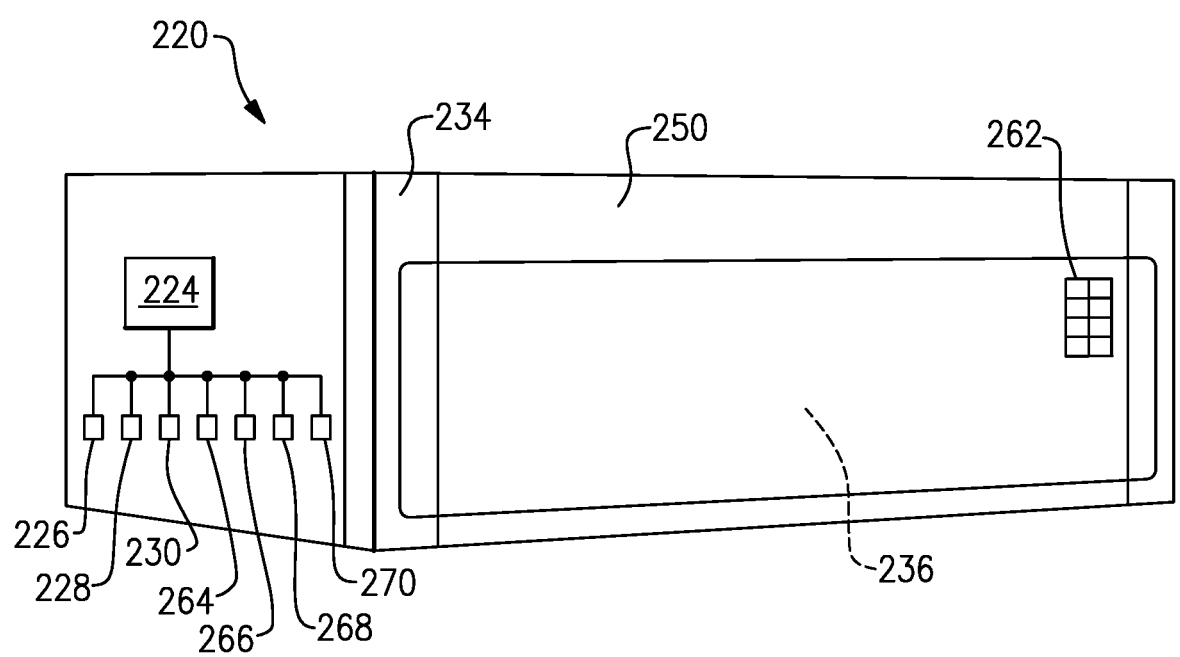
FIG. 5 illustrates another example device for disinfecting CPAP components and/or other equipment from a perspective view with a drawer of the device in a closed position.

The device 220 of FIG. 5 is another embodiment of this disclosure. The device 220 corresponds to the devices 20, 120, with like parts having reference numerals preappended with a "2."

In particular, the device 220 includes a base 234 and a drawer 254 configured to selectively open and close relative to the base 234 to provide access to a chamber 236 (shown in phantom). In FIG. 5, the drawer 254 is closed. The drawer 254 is configured to slide forward to open, in one example. The device 220 is not limited to sliding drawers, however, and could include a lid or door or some other selectively moveable closure.

In this example, the chamber 236 is relatively large and can hold a correspondingly large number of pieces of equipment. Such equipment may include CPAP components, medical devices, surgical instruments, etc. The chamber 236, in one example, has a volume of 7.5 cubic feet.

The device 220 includes a controller 224 in electric communication with the various components of the device 220. The device 220 also includes an interface 262, which may be a keypad or some other type of human-machine interface, configured to permit a user to adjust various operational settings of the device. Such settings may include maximum operating temperature, blower speed, maximum permitted ozone level, and/or cycle time.

Among other components, device 220 includes a heater 226, a blower 228, a UV light 230, a temperature sensor 264, an ozone generator 266, an ozone sensor 268, and a vacuum pump 270. Each of these components is illustrated schematically in FIG. 5. The controller 224 is configured to receive signals from each of these components and is further configured to issue commands to control the operation of these components.

In an example disinfection cycle, a user places one or more pieces of equipment into the chamber 236 by opening the drawer 250. The user then closes the drawer 250 and adjusts various operational settings, if desired, using the interface 262.

The example disinfection cycle includes a first phase which lasts a period of time, such as 7 minutes. During this first phase, the UV light 230, blower 228, and ozone generator 266 are on. In an example, the UV light 230 emits UV-C light at a wavelength of 254 nanometers (nm). Simultaneous with the emission of UV light, the ozone generator 266 generates ozone and the blower 228 circulates the ozone within the chamber 236. The level of ozone within the chamber 236 is maintained at a particular level based on feedback from the ozone sensor 268.

After completion of the first phase, the example disinfection cycle enters a second phase. During the second phase, the blower 228 continues to run, but the UV light 230 and ozone generator 266 are turned off. Further, the heater 226 is turned on and, based on feedback from the temperature sensor 264, the temperature of the chamber 236 is raised to a predetermined temperature, such as 190° F. (about 88° C.). In this example, the second phase lasts for a period of time, such as 7 minutes, beginning when the temperature of the chamber 236 reaches the predetermined temperature.

Following the second phase, the example disinfection cycle enters a third phase in which the heater 226 is turned off and the blower 228 continues to run to cool the equipment in the chamber 236. Near the end of the third phase, the vacuum pump 270 is turned on and evacuates the chamber 236 to the atmosphere. Evacuating the chamber 236 dramatically reduces, and in some examples completely rids, the chamber 236 of ozone. The level of ozone in the chamber 236 may be confirmed by the ozone sensor 268. In a particular aspect of this disclosure, the drawer 250 is locked during the disinfection cycle and only unlocks when either or both of the temperature and ozone levels are below predetermined levels. For instance, in one example, the drawer 250 is not unlocked until there is no detectable level of ozone in the chamber 236. The controller 224 is configured to instruct a locking mechanism to lock or unlock the drawer 250.

The combination of ozone, heat, and UV light makes the device 220 a particularly effective disinfecting tool. The device 220 incorporates certain features, such as the ozone sensor and vacuum pump, configured to properly manage ozone by using it as a disinfectant and without exposing it to the user. Further, the device 220 is particularly suited for use at a relatively large scale and in industrial or commercial settings, cleaning relatively large pieces of equipment and/or large quantities of equipment in laboratories and/or hospitals, as examples.

It should be understood that terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A device for disinfecting equipment, comprising:
   a chamber;
   an ultraviolet (UV) light source configured to emit UV light within the chamber;
   an ozone generator configured to generate ozone within the chamber;
   a control unit configured to activate the UV light source and the ozone generator simultaneously for a first period of time,
   a blower, the control unit configured to activate the blower for the first period of time;
   a heater;
   wherein, after the first period of time, the control unit is configured to activate the heater and cause the blower to continue to run for a second period of time,
   wherein the control unit is configured to activate the heater to raise a temperature of the chamber to a predetermined temperature and to maintain the chamber at the predetermined temperature for a second period of time,
   a vacuum pump;
   wherein, after the second period of time, the control unit is configured to deactivate the heater and cause the blower to continue to run for a third period of time, and
   wherein the control unit is configured to activate the vacuum pump during the third period of time.

2. The device as recited in claim 1, wherein the first period of time is seven minutes.

3. The device as recited in claim 2, wherein the UV light source emits UV light at a wavelength of 254 nanometers (nm).

4. The device as recited in claim 2, wherein the UV light source includes a 13 Watt UV-C bulb.

5. The device as recited in claim 1, wherein the UV light source emits UV-C light.

6. The device as recited in claim 1, wherein the second period of time is seven minutes.

7. The device as recited in claim 1, wherein the vacuum pump is activated near an end of the third period of time.

8. The device as recited in claim 1, further comprising:
   a base; and
   a closure moveable relative to the base between an open position and a closed position, wherein the base and closure provide boundaries of the chamber when the closure is in the closed position.

9. The device as recited in claim 8, wherein the closure is lockable relative to the base and is only unlocked when one or both of a temperature of the chamber and a level of ozone within the chamber are below predetermined thresholds.

10. The device as recited in claim 9, further comprising:
a temperature sensor;
an ozone sensor;
wherein the control unit is configured to interpret signals of the temperature sensor and the ozone sensor to determine a temperature of the chamber and a level of ozone within the chamber, respectively.

11. The device as recited in claim 9, wherein the closure is only unlocked when there is no detectable level of ozone within the chamber.

12. The device as recited in claim 1, wherein the chamber has a volume of 7.5 cubic feet.

13. The device as recited in claim 1, wherein the chamber is sized to receive at least one of CPAP components, medical devices, and surgical instruments.

14. The device as recited in claim 1, wherein, after the first period of time, the control unit is configured to deactivate the ozone generator and UV light source.

* * * * *